United States Patent [19]

Matsumoto

[11] 4,125,615

[45] Nov. 14, 1978

[54] 2-[4-(p-AMINOBENZYL)-1-PIPERAZINYL]-8-ETHYL-5,8-DIHYDRO-5-OXOPYRIDO[2,3-d]PYRIMIDINE-6-CARBOXYLIC ACID, ITS PHARMACEUTICALLY ACCEPTABLE SALT, PROCESS FOR ITS PRODUCTION AND USE THEREOF

[75] Inventor: Jun-ichi Matsumoto, Takatsuki, Japan

[73] Assignee: Dainippon Pharmaceutical Co., Ltd., Osaka, Japan

[21] Appl. No.: 817,539

[22] Filed: Jul. 20, 1977

[30] Foreign Application Priority Data

Jul. 22, 1976 [JP] Japan ................................. 51-87929

[51] Int. Cl.² .................. A61K 31/505; C07D 401/14
[52] U.S. Cl. ..................................... 424/251; 544/279
[58] Field of Search .................. 260/256.4 F; 424/251

[56] References Cited

U.S. PATENT DOCUMENTS

| | | | |
|---|---|---|---|
| 3,320,257 | 5/1967 | Lesher ........................... | 260/256.4 N |
| 3,673,184 | 6/1972 | Minami et al. ................. | 260/256.4 N |
| 3,770,742 | 11/1973 | Matsumoto et al. .......... | 260/256.4 N |
| 3,887,557 | 6/1975 | Minami et al. ................ | 260/256.4 N |
| 3,950,338 | 4/1976 | Pesson ........................... | 260/256.4 N |
| 3,992,380 | 11/1976 | Lesher et al. .................. | 260/256.4 N |

OTHER PUBLICATIONS

Shimizu, et al., "Antimicrobial Agents and Chemotherapy", 1970, pp. 117-122.
Shimizu, et al., "Antimicrobial Agents and Chemotherapy", vol. 9, No. 4, 1976, pp. 569-574.

*Primary Examiner*—Paul M. Coughlan, Jr.
*Assistant Examiner*—James H. Turnipseed
*Attorney, Agent, or Firm*—Wenderoth, Lind & Ponack

[57] ABSTRACT

2-[4-(p-Aminobenzyl)-1-piperazinyl]-8-ethyl-5,8-dihydro-5-oxopyrido-[2,3-d]pyrimidine-6-carboxylic acid, and its pharmaceutically acceptable salt. This novel compound can be prepared by reacting a compound of the formula

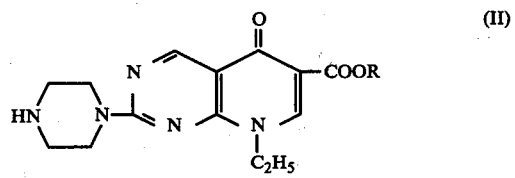

wherein R is a hydrogen atom or an alkyl group having 1 to 6 carbon atoms, with a compound of the formula

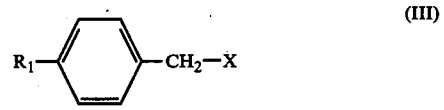

wherein $R_1$ is an amino group or a group convertible to the amino group, and X is a reactive moiety capable of splitting off together with the hydrogen atom at the 4-position of the 1-piperazinyl group of the compound of the formula (II). Pharmaceutical compositions containing aforesaid compounds as active ingredients are useful for treating a bacterial infection of man and other warm-blooded animals.

4 Claims, No Drawings

2-[4-(p-AMINOBENZYL)-1-PIPERAZINYL]-8-ETHYL-5,8-DIHYDRO-5-OXOPYRIDO[2,3-d]PYRIMIDINE-6-CARBOXYLIC ACID, ITS PHARMACEUTICALLY ACCEPTABLE SALT, PROCESS FOR ITS PRODUCTION AND USE THEREOF

This invention relates to 2-[4-(p-aminobenzyl)-1-piperazinyl]-8-ethyl-5,8-dihydro-5-oxopyrido[2,3-d]-pyrimidine-6-carboxylic acid of the following formula (I) that is useful as an antibacterial agent, its pharmaceutically acceptable salt, processes for producing these compounds, and to preparations containing them;

(I)

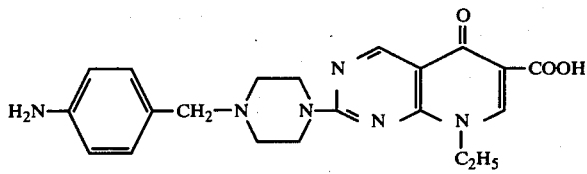

The compounds of the present invention are excellent antibacterial agents having a broad antibacterial spectrum.

It has been well known that a variety of 2-substituted amino-8-alkyl-5,8-dihydro-5-oxopyrido[2,3-d] pyrimidine-6-carboxylic acids exhibit excellent effects on Gram-negative bacterial infections (U.S. Pat. Nos. 3,320,257, 3,673,184, 3,770,742, 3,887,557, 3,950,338, etc.). However, their antibacterial activities against Gram-positive bacteria are not entirely satisfactory and therefore their relatively narrow antibacterial spectra have been pointed out as their disadvantages. For instance, 2-pyrrolidino- and 2-(1-piperazinyl)-8-ethyl-5,8-dihydro-5-oxopyrido[2,3-d]pyrimidine-6-carboxylic acids have been used practically for the treatment of bacterial infections under the generic names of piromidic acid and pipemidic acid, respectively. However, it has been reported that they exhibit only extremely weak effect on systemic infection by *Staphylococcus aureus* [Antimicrob. Agents Chemother. 117–122(1970) and ibid, 9, 569–574(1976)].

U.S. Pat. Nos. 3,887,557 and 3,950,338 disclose 2-(4-benzyl-1-piperazinyl)-, 2-[4-(p-methoxybenzyl)-1-piperazinyl]-, and 2-[4-(p-chlorobenzyl)-1-piperazinyl]-8-ethyl-5,8-dihydro-5-oxopyrido[2,3-d]pyrimidine-6-carboxylic acids. Though these compounds exhibit relatively strong in vitro activities against *Staphylococcus aureus*, their in vivo activities against it are weak.

As a result of intensive researches, the inventor of this invention has discovered surprisingly that the compound expressed by the aforementioned formula (I) and its pharmaceutically acceptable salts exhibit extremely satisfactory antibacterial activities, both in vitro and in vivo, against Gram-positive bacteria, especially against *Staphylococcus aureus*, as well as against Gram-negative bacteria and, in addition, they have low toxicity.

It is therefore an object of the present invention to provide novel compounds that have a broad antibacterial spectrum as well as excellent antibacterial activities.

Another object of the invention is to provide a process for producing the abovementioned novel compounds.

Still another object of the invention is to provide an antibacterial agent or a pharmaceutical composition containing such a novel compound as its active ingredient.

Still another object of the invention is to provide a method of treating bacterial infections of man and other warm-blooded animals such for example as domestic animals, poultry, pets, and the like, using the abovementioned novel compounds.

These and many other objects and advantages of the invention will become more apparent from the following detailed description thereof.

The compound (I) of the present invention is obtained by reacting a compound of the formula (II)

(II)

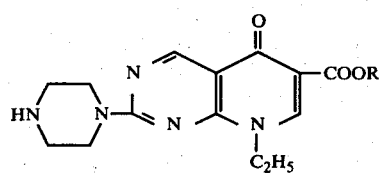

wherein R is a hydrogen atom or an alkyl group of 1 to 6 carbon atoms, with a compound of the formula (III)

(III)

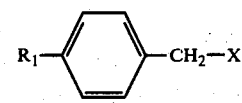

wherein $R_1$ is an amino group or a group convertible to the amino group such as an acylamino group, a nitro group or a nitroso group, and X is a reactive moiety capable of splitting off together with the hydrogen atom at the 4-position of the 1-piperazinyl group of the compound of the formula (II), and if necessary, hydrolyzing or/and reducing the reaction product.

In the abovementioned formula (III), examples of the acyl group of the acylamino group for $R_1$ include $C_1$-$C_6$ carbonic or carboxylic acid residues, which may be substituted by a halogen, such as a lower alkanoyl group, e.g. formyl, acetyl, trifluoroacetyl, or propionyl; a lower alkoxycarbonyl group, e.g. methoxycarbonyl or ethoxycarbonyl; and a phenyl-substituted lower alkoxycarbonyl group, e.g. benzyloxycarbonyl.

Examples of the reactive moiety for X in the formula (III) include a halogen atom such as chlorine, bromine or iodine; an arylsulfonyloxy group such as p-toluenesulfonyloxy or benzenesulfonyloxy; and a lower alkylsulfonyloxy group such as methanesulfonyloxy or ethanesulfonyloxy.

The reaction between the compound of the formula (II) and the compound of the formula (III) is generally carried out in an inert solvent in the preferably presence of a base. Examples of the solvent for this purpose are dimethylformamide, dimethyl sulfoxide and alcohols such as ethanol, and dimethylformamide is preferred among these solvents. Examples of the base are alkali carbonates such as sodium carbonate and potassium carbonate; alkali hydrogen carbonates such as sodium hydrogen carbonate and potassium hydrogen carbonate; alkali metal hydrides such as sodium hydride; and tertiary amines such as trimethylamine, triethylamine and N,N-dimethylaniline.

The amount of the compound of the formula (III) is not critical. Generally the compound (III) is used in an amount of from about 1 to about 3 moles per mole of the compound (II), preferably in a slightly excessive amount, e.g., from about 1.5 to about 2 moles per mole of the compound (II). The reaction temperature ranges from room temperature to about 150° C., preferably from about 50° to about 120° C.

When the reaction between the compounds (II) and (III) gives a product of the following formula (I') having a hydrogen or an alkyl group as R and an acylamino group as $R_1$, it is hydrolyzed in a customary manner to give the compound (I) of the present invention;

with acids, e.g. hydrochloric acid, sulfuric acid, acetic acid, etc.

Preferred examples of solvents used for the catalytic reduction are ethanol, dioxane and acetic acid, and water and hydrous ethanol are suitable solvents for the reducing method that uses the abovementioned metal and acid in combination. The reaction temperature ranges from room temperature to about 120° C.

Additionally, the starting compound (II) may be produced in accordance with the production method disclosed in U.S. Pat. Nos. 3,887,577, 3,950,338, etc.

Since the compound of the aforementioned formula (I) produced in this manner is amphoteric, it may be isolated by adjusting the pH of the system of the reaction product to about 6.5 - about 7.5 and collecting the solid precipitate. The compound thus obtained can be purified by recrystallization from solvents such as alco-

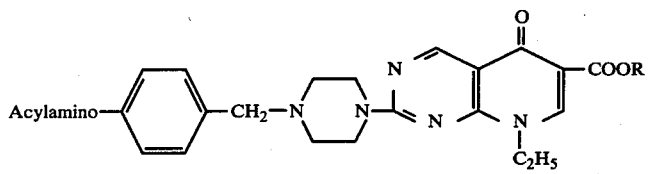

(I')

wherein R has the same meaning as defined in the formula (II).

The hydrolyzing reaction is performed, for example, by heating the resulting compound (I') preferably to about 70° - about 120° C. in water or in a mixture of water and a polar solvent (e.g. ethanol, isopropanol, acetic acid, etc.) in the presence of an acid or of a base. Examples of the acid are mineral acids such as hydrochloric acid, hydrobromic acid, hydriodic acid, sulfuric acid and phosphoric acid, and organic acids such as p-toluenesulfonic acid. Examples of the base are alkali metal hydroxides such as sodium hydroxide and potassium hydroxide, and alkali carbonates such as sodium carbonate and potassium carbonate.

When the reaction between the compounds (II) and (III) affords a product of the following formula (I'') having a nitro group or a nitroso group as $R_1$, the compound (I) of the present invention can be obtained by reducing the nitro group or the nitroso group in the compound (I'');

hols (e.g. ethanol), hydrous dimethylformamide, hydrous acetic acid, acetonitrile and the like. Alternatively, the resulting compound may be purified by reprecipitation by dissolving it in an aqueous alkaline solution or an aqueous solution of a mineral acid or an organic acid, and adding a mineral acid or an organic acid for the former and an alkali in the case of the latter.

In the process of the present invention, the compound of the formula (I) may be obtained either in the free form or in the salt form by properly selecting the reaction conditions. The salt can be converted to the free form by neutralizing it in a customary manner. On the other hand, the compound in the free form may be led to an acid addition salt or an alkali metal salt by treating it with various pharmaceutically acceptable acids or alkali metal compounds in a customary manner.

Specific examples of the acid for the abovementioned purpose include inorganic and organic acids such as hydrochloric acid, hydrobromic acid, nitric acid, sulfuric acid, phosphoric acid, methanesulfonic acid, acetic

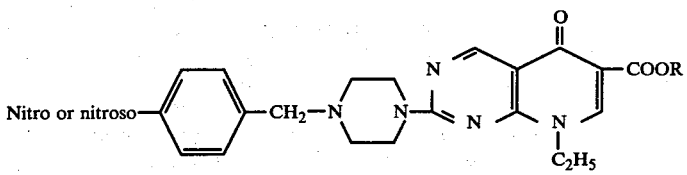

(I'')

wherein R has the same meaning as defined in the formula (II).

When R is an alkyl group in the abovementioned compound (I''), the compound (I) of this invention can be obtained by hydrolyzing it in the same way as mentioned above before or after conversion of the nitro group or the nitroso group to the amino group.

The abovementioned reducing reaction is performed in accordance with conventional methods of reducing a nitro group or a nitroso group to an amino group. Examples of such reducing methods are a catalytic reducing method using a reducing catalyst such as palladium-on-charcoal or a Raney nickel, and a reducing method using the combination of metals, e.g. iron, zinc, tin, etc., acid, citric acid, maleic acid, fumaric acid, succinic acid, lactic acid, malic acid, tartaric acid and the like. Specific examples of the alkali metal compound include alkali metal hydroxides such as sodium hydroxide, and potassium hydroxide, and alkali metal alcoholates such as sodium methylate.

The antibacterial activities and toxicity of the compound of this invention are shown in Tables I to V together with those of the known compounds described above.

The compounds tested are as follows:
Compound AT-1826:
  The compound of this invention Compound PA:
 2-Pyrrolidino-8-ethyl-5,8-dihydro-5-oxopyrido [2,3-d]pyrimidine-6-carboxylic acid [disclosed in U.S. Pat. No. 3,673,184]

Compound PPA:
 2-(1-Piperazinyl)-8-ethyl-5,8-dihydro-5-oxopyrido [2,3-d]pyrimidine-6-carboxylic acid [disclosed in U.S. Pat. Nos. 3,887,557 and 3,950,338]

Compound 1:
 2-(4-Benzyl-1-piperazinyl)-8-ethyl-5,8-dihydro-5-oxopyrido[2,3-d]-pyrimidine-6-carboxylic acid [disclosed in U.S. Pat. Nos. 3,887,557 and 3,950,338]

Compound 2:
 2-[4-(p-Methoxybenzyl)-1-piperazinyl]-8-ethyl-5,8-dihydro-5-oxopyrido[2,3-d]pyrimidine-6-carboxylic acid [disclosed in U.S. Pat. Nos. 3,887,557 and 3,950,338]

Compound 3:
 2-[4-(p-Chlorobenzyl)-1-piperazinyl]-8-ethyl-5,8-dihydro-5-oxopyrido[2,3-d]pyrimidine-6-carboxylic acid [disclosed in U.S. Pat. No. 3,950,338]

(1) In vitro antibacterial activity against 9 strains of bacteria (Gram-positive bacteria: 4 strains, Gram-negative bacteria: 5 strains)

The test compounds were dissolved in distilled water at a concentration of 1 mg/ml with equimolar NaOH. Then graded concentrations (300, 100, 30, 10, 3 μg/ml, etc.) were made by serial dilution with distilled water. Each solution of test compound (0.5 ml) was pipetted into 4.5 ml of medium in a tube. The media used were Brain Heart Infusion Broth, pH 7.4, for Streptococcus and nutrient broth [10 g of Polypepton, 10 g of Meat Extract, and 2.5 g of NaCl in 1 liter of distilled water], pH 7.0, for the other bacteria. One drop of a bacterial suspension freshly cultured and diluted so as to contain 10 to 100 minimal growing units in the medium was inoculated into the tube. The tubes were incubated at 37° C. for 48 hours. The minimal inhibitor concentration (MIC) was defined as the lowest concentration in which no visible growth of the bacteria was detected.

Table I

| Compound Strain | MIC (μg/ml) | | | | | |
|---|---|---|---|---|---|---|
| | At-1826 | PA | PPA | 1 | 2 | 3 |
| Staphylococcus aureus Terajima | 3 | 10 | 30 | 10 | 10 | 10 |
| Staphylococcus aureus No. 10 | 3 | 10 | 10 | 10 | 10 | 10 |
| Staphylococcus aureus No. 50774 | 1 | 10 | 10 | 3 | 3 | 3 |
| Streptococcus pyogenes A65 | 30 | 300 | 100 | 100 | 100 | 30 |
| Escherichia coli K-12 | 1 | 1 | 1 | 3 | 3 | 10 |
| Escherichia coli P-5101 | 3 | 10 | 1 | 10 | 10 | 30 |
| Proteus vulgaris OX-19 | 3 | 1 | 3 | 3 | 10 | 10 |
| Shigella sonnei EW33 | 1 | 3 | 1 | 3 | 3 | 3 |
| Salmonella typhimurium S-9 | 3 | 3 | 1 | 3 | 3 | 10 |

(2) In vivo efficacy against the intravenous infection of mice by *Staphylococcus aureus* No. 50774

Each group of 8 male mice (ddY strain, approximately 20 g) was intravenously infected with 6 $LD_{50}$ of *Staphylococcus aureus* No. 50774 in 0.85% saline. The test compounds were each suspended in 0.2% carboxymethyl cellulose and administered orally in graded doses (200, 100, 50, 25, 12.5, 6.3, 3.1 mg/kg, etc.) to the infected mice twice, about 5 minutes and 6 hours after infection. Survival rates were determined after 2 weeks and the $ED_{50}$ was calculated in accordance with Probit method.

Table II

| Compound | $ED_{50}$ (mg/kg) |
|---|---|
| AT-1826 | 7.2 |
| PA | >200 |
| PPA | 237.5 |
| 1 | ca. 50 |
| 2 | 54.5 |
| 3 | >100 |

(3) In vivo efficacy against the intraperitoneal infection of mice by *Streptococcus pyogenes* A65

Each group of 8 male mice (ddY strain, approximately 20 g) was intraperitoneally infected with 4 $LD_{50}$ of *Streptococcus pyogenes* A65 suspended in Brain Heart Infusion Broth. The subsequent procedures were the same as those described in (2).

Table III

| Compound | $ED_{50}$ (mg/kg) |
|---|---|
| AT-1826 | 47.7 |
| PA | >100 |
| PPA | >100 |
| 1 | >100 |
| 2 | >100 |
| 3 | >100 |

(4) In vivo efficacy against the intraperitoneal infection of mice by *Escherichia coli* p-5101

Each group of 8 male mice (ddY strain, approximately 20 g) was intraperitoneally infected with 9 $LD_{50}$ of *Escherichia coli* p-5101 suspended in Trypto-Soy Broth supplemented with 4% gastric mucin. The subsequent procedures were the same as those described in (2).

Table IV

| Compound | $ED_{50}$ (mg/kg) |
|---|---|
| AT-1826 | 35.6 |
| PA | 36.6 |
| PPA | 21.2 |

(5) Acute toxicity in mice

Female ddY strain mice, weighing 25 to 33 g, were used. Test compounds were suspended in 0.2% carboxymethyl cellulose for oral administration, and dissolved in NaOH solution (final pH 8.8–9.2) for intravenous administration. After administering test compounds, the mice were observed for 7 days and then the $LD_{50}$ was calculated according to Behrens-Kaerber method.

Table V

| Compound | $LD_{50}$ (mg/kg) | |
|---|---|---|
| | p* | iv** |
| AT-1826 | >2000 | 354 |
| PA | >2000 | 268 |
| PPA | >2000 | 707 |

*oral administration
**intravenous administration

As can be appreciated clearly from the experimental results illustrated above, the compound of the present invention exhibits excellent antibacterial activities against Gram-positive and Gram-negative bacteria and has low toxicity. Hence, the present compound may be used advantageously for the treatment of bacterial infections of warm-blooded animals including man as an antibacterial agent. A preferred route of administration of the present compound is peroral or intrarectal.

The dosage of the compound (I) or its salt of the present invention may be selected properly in accordance with body weight, age, symptoms and administration route and the like. It is generally in the range of from about 100 mg to about 5g/day, preferably from about 200 mg to about 3g/day for adults. If necessary, the compound (I) or its salt may be administered several times a day dividedly.

The compound (I) or its salt of the present invention may be applied in the form of a pharmaceutical preparation which contains the compound (I) or its salt in admixture with a pharmaceutically acceptable carrier. Examples of the carrier are those solid or liquid carriers which are used generally in the field of pharmaceutical preparations and which do not react with the compound (I) or its salt. More specifically, examples of these carriers are such solid carriers as gelatin, lactose, white sugar, starch, arabic gum, tragacanth, microcrystalline cellulose, sodium carboxymethyl cellulose, calcium carboxymethyl cellulose hydroxypropyl cellulose, polyvinylpyrrolidone, light anhydrous silicic acid, magnesium stearate and talc; and such liquid carriers as water, a physiological saline solution, vegetable oils, benzyl alcohol and propylene glycol.

Examples of the preparation include solid preparations such as tablets, capsules, troches, granules, powders and suppositories; and liquid preparations such as syrups, elixirs, emulsions, suspensions and injections. These preparations may be produced by conventional methods. The liquid preparations may be in the form of a solution or a suspension in the abovementioned liquid carrier. Furthermore, the tablets may be coated by known methods.

Though varying to some extents depending on types, these preparations may contain about 10 to about 60% by weight of the active compound. The preparations may also contain other therapeutically effective compounds.

The following examples illustrate the present invention in further detail without, however, limiting the invention thereto.

EXAMPLE 1

2-[4-(p-Acetamidobenzyl)-1-piperazinyl]-8-ethyl-5,8-dihydro-5-oxopyrido[2,3-d]pyrimidine-6-carboxylic acid:-

To a suspension of 35.3 g of 2-(1-piperazinyl)-8-ethyl-5,8-dihydro-5-oxopyrido[2,3-d]pyrimidine-6-carboxylic acid in 500 ml of dimethylformamide was added a solution of 39.0 g of potassium carbonate in 50 ml of water and then 39.5 g of p-acetamidobenzyl bromide. The mixture was heated at 80°–90° C. for 1.5 hours with stirring. After removal of a small amount of the insoluble material by filtration, the filtrate was concentrated to dryness under reduced pressure and the residue was dissolved in 100 ml of water. The solution was adjusted to pH 7.0 with acetic acid. The precipitate was collected by filtration and recrystallized from a mixture of dimethylformamide and ethanol to give the product (42.3 g), m.p. 216.5°–219° C.

EXAMPLE 2

2-[4-(p-Aminobenzyl)-1-piperazinyl]-8-ethyl-5,8-dihydro-5-oxopyrido[2,3-d]pyrimidine-6-carboxylic acid:-

A solution of 32.0 g of 2-[4-(p-acetamidobenzyl)-1-piperazinyl]-8-ethyl-5,8-dihydro-5-oxopyrido[2,3-d]pyrimidine-6-carboxylic acid in a mixture of 580 ml of 13% hydrochloric acid and 140 ml of 50% acetic acid was heated at 90° C. for 70 minutes with stirring and concentrated to dryness under reduced pressure. The residue was dissolved in 200 ml of water, the solution made alkaline with 20 ml of a 50% sodium hydroxide solution, and adjusted to pH 7.5 with acetic acid. The crystalline precipitate was collected and recrystallized from ethanol to give the product (22.6 g), m.p. 198°–201° C.

EXAMPLE 3

2-[4-(p-Nitrobenzyl)-1-piperazinyl]-8-ethyl-5,8-dihydro-5-oxopyrido[2,3-d]pyrimidine-6-carboxylic acid:-

A mixture of 2.0 g of 2-(1-piperazinyl)-8-ethyl-5,8-dihydro-5-oxopyrido[2,3-d]pyrimidine-6-carboxylic acid, 1.34 g of triethylamine, 2.14 g of p-nitrobenzyl bromide, and 50 ml of dimethylformamide was heated at 90° C. for 14 hours with stirring and concentrated to dryness under reduced pressure. Addition of 50 ml of water to the residue resulted in the separation of a solid, which was collected and recrystallized from dimethylformamide to give the product (2.02 g), m.p. 259°–261° C.

EXAMPLE 4

2-[4-(p-Aminobenzyl)-1-piperazinyl]-8-ethyl-5,8-dihydro-5-oxopyrido[2,3-d]pyrimidine-6-carboxylic acid:-

A solution of 3.40 g of 2-[4-(p-nitrobenzyl)-1-piperazinyl]-8-ethyl-5,8-dihydro-5-oxopyrido[2,3-d]pyrimidine-6-carboxylic acid in 200 ml of acetic acid was hydrogenated over 0.55 g of 5% palladium-on-charcoal catalyst at room temperature until 3 mole equivalents of hydrogen were absorbed. The catalyst was removed by filtration and the filtrate was concentrated to dryness under reduced pressure. To the residue was added 30 ml of water and the resulting solution was neutralized with a saturated sodium bicarbonate solution. The crystalline precipitate was collected by filtration and dissolved with warming in 100 ml of ethanol. After removal of the insoluble material by filtration, the filtrate was kept under cooling to give the crude precipitated product (1.80 g), which was dissolved in a minimum amount of chloroform and chromatographed on 14 g of silica gel, using chloroform-methanol (a 50:1 ratio by volume) as eluent. Fractions containing the desired product were pooled and concentrated to dryness. The resulting solid was recrystallized from ethanol to give the pure product, m.p. 198°–201° C.

EXAMPLE 5

2-[4-(p-Aminobenzyl)-1-piperazinyl]-8-ethyl-5,8-dihydro-5-oxopyrido[2,3-d]pyrimidine-6-carboxylic acid hydrochloride:-

2-[4-(p-Aminobenzyl)-1-piperazinyl]-8-ethyl-5,8-dihydro-5-oxopyrido[2,3-d]pyrimidine-6-carboxylic acid (3.0 g) was dissolved in 300 ml of ethanol by heating at 80° C. To the hot solution was added 0.5 ml of concentrated hydrochloric acid and the mixture was allowed to stand in a refrigerator. The resulting precipitate was collected by filtration and recrystallized twice from ethanol containing a small amount of concentrated hydrochloric acid to give the product (2.2 g), m.p. above 300° C.

EXAMPLE 6

2-[4-(p-Aminobenzyl)-1-piperazinyl]-8-ethyl-5,8-dihydro-5-oxopyrido[2,3-d]pyrimidine-6-carboxylic acid methanesulfonate was prepared by the same manner as in Example 5 using methanesulfonic acid in place of hydrochloric acid. m.p. above 300° C., decomposing from about 220° C. without melting.

EXAMPLE 7

Potassium 2-[4-(p-aminobenzyl)-1-piperazinyl]-8-ethyl-5,8-dihydro-5-oxypyrido[2,3-d]pyrimidine-6-carboxylate:-

To a hot solution of 4.0 g of 2-[4-(p-aminobenzyl)-1-piperazinyl]-8-ethyl-5,8-dihydro-5-oxopyrido[2,3-d]pyrimidine-6-carboxylic acid in 400 ml of ethanol was added a solution of 0.64 g of potassium ethoxide in 100 ml of ethanol. The mixture was concentrated to about 100 ml and cooled. The resulting precipitate was collected and recrystallized from ethanol to give the product (3.9 g), m.p. 268°–276° C. (decomp.).

EXAMPLE 8

2-[4-(p-Aminobenzyl)-1-piperazinyl]-8-ethyl-5,8-dihydro-5-oxopyrido[2,3-d]pyrimidine-6-

| | |
|---|---|
| carboxylic acid | 250 g |
| Lactose | 64 g |
| Calcium carboxymethyl cellulose | 45 g |
| Microcrystalline cellulose | 50 g |
| Polyvinylpyrrolidone | 7 g |
| Magnesium stearate | 4 g |

The above components were blended, granulated and made into tablets in a conventional manner. Thus, 1,000 tablets each weighing 420 mg were formed.

EXAMPLE 9

2-[4-(p-Aminobenzyl)-1-piperazinyl]-8-ethyl-5,8-dihydro-5-oxopyrido[2,3-d]pyrimidine-6-

| | |
|---|---|
| carboxylic acid | 250 g |
| Starch | 100 g |
| Lactose | 70 g |
| Talc | 27 g |
| Magnesium stearate | 3 g |

The above components were blended, granulated and filled into 1,000 capsules in accordance with conventional methods.

What we claim is:

1. 2-[4-(p-Aminobenzyl)-1-piperazinyl]-8-ethyl-5,8-dihydro-5-oxopyrido-[2,3-d]pyrimidine-6-carboxylic acid.

2. A pharmaceutically acceptable salt of 2-[4-(p-aminobenzyl)-1-piperazinyl]-8-ethyl-5,8-dihydro-5-oxopyrido[2,3-d]pyrimidine-6-carboxylic acid.

3. A pharmaceutical composition comprising from 10 to 60% by weight of 2-[4-(p-aminobenzyl)-1-piperazinyl]-8-ethyl-5,8-dihydro-5-oxopyrido[2,3-d]pyrimidine-6-carboxylic acid or a pharmaceutically acceptable salt thereof in admixture with a pharmaceutically acceptable carrier.

4. A method of treating a bacterially infected patient which comprises administering to such patient 2-[4-(p-aminobenzyl)-1-piperazinyl]-8-ethyl-5,8-dihydro-5-oxopyrido[2,3-d]pyrimidine-6-carboxylic acid or a pharmaceutically acceptable salt thereof in a daily dose of from 100 mg to 5 g for adult.

* * * * *